United States Patent
Raths et al.

(10) Patent No.: US 6,429,324 B1
(45) Date of Patent: Aug. 6, 2002

(54) METHOD FOR PRODUCING ALKOXYLATED DIMER FATTY ACIDS

(75) Inventors: Hans-Christian Raths, Monheim; Frank Bongardt, Meerbusch; Ansgar Behler, Bottrop; Juergen Roeder, Duesseldorf, all of (DE)

(73) Assignee: Cognis Deutschland and GmbH, Duesseldorf (DE)

( * ) Notice: Subject to any disclaimer, the term of this patent is extended or adjusted under 35 U.S.C. 154(b) by 03 days.

(21) Appl. No.: 09/581,439

(22) PCT Filed: Dec. 4, 1998

(86) PCT No.: PCT/EP98/07907

§ 371 (c)(1),
(2), (4) Date: Aug. 18, 2000

(87) PCT Pub. No.: WO99/31040

PCT Pub. Date: Jun. 24, 1999

(30) Foreign Application Priority Data

Dec. 13, 1997 (DE) .......................................... 197 55 559

(51) Int. Cl.$^7$ .............................................. C07C 51/00
(52) U.S. Cl. ...................................................... 554/149
(58) Field of Search ............................. 554/149, 25, 26

(56) References Cited

U.S. PATENT DOCUMENTS

| | | |
|---|---|---|
| 3,884,946 A | 5/1975 | Sung et al. |
| 4,557,846 A | 12/1985 | Wisotsky |
| 4,609,376 A | 9/1986 | Craig et al. |
| 4,684,473 A | 8/1987 | Bock et al. |
| 4,885,008 A | 12/1989 | Ishizaki et al. |
| 5,936,107 A | 8/1999 | Raths et al. |

FOREIGN PATENT DOCUMENTS

| | | |
|---|---|---|
| DE | 20 24 050 A | 12/1971 |
| DE | 35 34 442 A1 | 4/1987 |
| EP | 0 178 913 A | 4/1986 |
| EP | 0 608 149 A1 | 7/1994 |

OTHER PUBLICATIONS

Bartholome et al., "Ullmanns Encyklopädie technischen Chemie", Band 4, Verlag Chemie, Weinheim, (1976), p. 540.
Behr, et al., Fat. Sci. Technol., 93, (1991), pp. 340–345.
Spiteller, Fat. Sci. Technol., 94, (1992), pp. 41–46.
Daute, et al., Fat Sci. Technol., 95, (1993), pp. 91–94.
Otter, Fette, Seifen, Anstrichmittel (Fats, Soaps, Coatings), 72, (1970), p. 667.
Ishizaki et al, EP 326356, , A method for improving cold flow of hydrocarbon fuel oils, see abs and citation, AN 1989.236489 CAPLUS, Aug. 1999.*

* cited by examiner

Primary Examiner—Deborah D. Carr
(74) Attorney, Agent, or Firm—John E. Drach; Aaron R. Ettelman

(57) ABSTRACT

Processes for preparing alkylene glycol esters of dimer fatty acids according to the general formula (I):

$$H-(OR)_n-O(O)C-R^1-C(O)O-(RO)_n-H \quad (I)$$

wherein $R^1$ represents a hydrocarbon radical of a dimer fatty acid having from about 24 to about 44 carbon atoms, and each R independently represents an alkyl radical having from about 2 to about 3 carbon atoms, and each n independently represents a number of from about 0.25 to about 3.0, are described. The processes include: (a) providing dimer fatty acids; (b) providing an alkylene oxide; and (c) reacting the dimer fatty acids and the alkylene oxide, in the presence of a catalytically-effective amount of at least one alkanolamine.

20 Claims, No Drawings

METHOD FOR PRODUCING ALKOXYLATED DIMER FATTY ACIDS

This application is a 371 of PCT/EP98/07907 filed Dec. 4, 1998.

BACKGROUND OF THE INVENTION

The addition of alkylene oxides to CH-acidic compounds such as, for example, fatty alcohols, alkylphenols, fatty amines or else fatty acids is one of the large-scale established methods for producing nonionic surfactants. These reactions are usually carried out in the presence of homogeneous basic catalysts, such as, for example, sodium hydroxide or sodium methoxide. However, the alkoxylation is not a very selective reaction, meaning that in practice, particularly at low alkoxylation ratios, the maximum resulting homolog distribution does not correspond to the average degree of alkoxylation.

Attempts have been made to counter this undesired effect by using catalysts which have higher selectivity and lead in total to alkoxylates, specifically ethoxylates, having a narrower ("narrowed") homolog distribution; these products are frequently also referred in the literature as "narrow-range ethoxylates". Suitable homogeneous catalysts for this purpose are, preferably, alkaline earth metal salts, such as, for example, barium phosphate or strontium ether carboxylates. Heterogeneous catalysts, such as, for example, calcined hydrotalcites, are also suitable for this purpose.

With regard to the ethoxylation of fatty acids, the efforts in the prior art nevertheless continue to be unsatisfactory. Particularly in the case of fatty acids with low degrees of ethoxylation, specifically fatty acid +1EO adducts, which are interesting as precursors for the synthesis of ether sulfate surfactants having isethionate-type structure, satisfactory selectivities have not been established. In addition to an undesired proportion of more highly ethoxylated homologs, significant amounts of polyethylene glycol and diesters, in particular, are also formed in the process. Even the method as in U.S. Pat. No. 3,884,946 (Henkel), which recommends the use of amines as catalysts for this purpose, produces fatty acids with a low degree of ethoxylation in yields significantly below 90% of theory. Better yields can be obtained for fatty acids with a low degree of ethoxylation if the method is carried out as in U.S. Pat. No. 5,936,107, issued Aug. 10, 1999 (Henkel).

In addition to an undesired proportion of more highly ethoxylated homologs, significant amounts of polyethylene glycol and diesters, in particular, are also formed in the process. Even the method as in U.S. Pat. No. 3,884,946 (Henkel), which recommends the use of amines as catalysts for this purpose, produces fatty acids with a low degree of ethoxylation in yields significantly below 90% of theory. Better yields can be obtained for fatty acids with a low degree of ethoxylation if the method is carried out as in American patent application Ser. No. 08/767,123.

According to this method, the ethoxylation is carried out in the presence of alkanolamines as catalysts and produces significantly higher yields.

According to European Laid-open Patent Specification EP-A-178 913, it is possible to alkoxylate not only straight-chain fatty acids, but also branched neocarboxylic acids having a tertiary carbon atom in an adjacent position to the carboxyl group in the presence of amines such as diethanolamine and triethanolamine with increased selectivity. However, in order to obtain good yields with this method, relatively high temperatures in the range of from 140 to 185° C. are necessary.

According to the cited prior art, the problem of selectivity during alkoxylation has only been investigated for monomeric carboxylic acids. However, to date, the problem of selective alkoxylation in the case of oligomeric carboxylic acids, in particular in the case of dimer fatty acids, has not been considered. There was therefore a need to provide a selective method also for the alkoxylation of dimer fatty acids.

BRIEF SUMMARY OF THE INVENTION

Consequently, the object of the present invention was to provide an improved homogeneously catalyzed method for producing alkylene glycol esters of dimer fatty acids, specifically dimer fatty acids with a low degree of alkoxylation, which has improved selectivity.

Surprisingly, we were able to achieve the object by alkanolamines, specifically triethanolamine, being present as catalyst during the alkoxylation of the dimer fatty acids. This process is particularly suitable for the preparation of dimer fatty acids which have a low degree of alkoxylation.

The present invention provides a method for producing alkylene glycol esters of dimer fatty acids by addition of alkylene oxide to dimer fatty acids in the presence of alkanolamines as catalysts.

For the purposes of the present invention, the terms "alkoxylated dimer fatty acids" and "alkylene glycol esters of dimer fatty acids" are used synonymously.

DETAILED DESCRIPTION OF THE INVENTION

Dimer Fatty Acids

For the purposes of the invention, the term dimer fatty acids means technical-grade mixtures obtained by oligomerization of unsaturated fatty acids or methyl esters thereof.

The oligomerization of unsaturated fatty acids is a known electrocyclic reaction reported in review articles, for example, by A. Behr in Fat Sci. Technol. 93, 340 (1991), G. Spiteller in Fat Sci. Technol. 94, 41 (1992) or P. Daute et al. in Fat Sci. Technol. 95, 91 (1993). During the oligomerization, on average two to three fatty acids come together and form dimers or trimers, which have predominantly cycloaliphatic structures. As well as the fraction of dimers and trimers, a so-called monomer fraction is obtained which contains unreacted starting materials and branched monomers formed in the course of the reaction by isomerization. In addition, there is of course also a fraction of higher oligomers, although this is usually not of any great significance. The oligomerization can be carried out thermally or in the presence of noble metal catalysts. The reaction is preferably carried out in the presence of clay earths, such as, for example, montmorillonite [cf. Fette, Seifen, Anstrichmitt. [Fats, Soaps, Coatings] 72, 667 (1970)]. The content of dimers and trimers or the extent of the monomer fraction can be controlled by the reaction conditions. Finally, technical-grade mixtures can be purified, including by distillation.

Suitable starting materials for the oligomerization are technical-grade unsaturated fatty acids having 12 to 22 carbon atoms, preferably 16 to 18 carbon atoms. Typical examples are palmoleic acid, oleic acid, elaidyl acid, petroselinyl acid, linoleic acid, linolenic acid, conjuene fatty acid, elaeostearic acid, ricinoleic acid, gadoleic acid, erucic acid, and technical-grade mixtures thereof with saturated fatty acids. Typical examples of suitable technical-grade mixtures are nonhydrogenated cleavage fatty acids of natural triglycerides having iodine numbers in the range from 40 to 140, such as, for example, palm fatty acid, tallow fatty acid, rape oil fatty acid, sunflower fatty acid and the like. Preference is given to cleavage fatty acids with a high content of oleic acid.

In addition to the fatty acids, it is also possible to dimerize the esters thereof, preferably methyl esters. It is likewise possible to oligomerize the acid and to convert it to the methyl ester prior to hydrogenation. Conversion of the ester group to the acid group is carried out in a manner known per se.

Dimer fatty acids which are particularly preferred for the purposes of the invention are obtained by oligomerization of technical-grade oleic acid and preferably have a dimer content of from 50 to 99% by weight, and a polymer content (including trimer content) of from 1 to 50% by weight. The content of monomers can be from 1 to 15% by weight and if necessary lowered by distillation. Particular preference is given to dimer fatty acids which are obtained by oligomerization of technical-grade oleic acid and have a dimer content of from 70 to 85% by weight, a polymer content of from 10 to 20% by weight and a monomer content of from 5 to 15% by weight. The % by weight are based here on the total amount of dimer fatty acid.

Alkanolamines

Typical examples of alkanolamines which are suitable as homogeneous basic catalysts are monoethanolamine, diethanolamine and, preferably, triethanolamine. Also suitable as catalysts are amines based on diols, preferably diglycolamine. The alkanolamines are usually used in amounts of from 0.05 to 5% by weight, preferably 0.1 to 1.5% by weight, based on the dimer fatty acids.

Alkoxylation

The alkoxylation can be carried out in a manner known per se and is described below using ethoxylation as an example.

Usually, the dimer fatty acid and the catalyst are initially introduced into a stirred autoclave which has been freed from traces of water prior to the reaction by alternately evacuating, preferably at temperatures in the range from 80 to 120° C., and flushing with nitrogen. The dimer fatty acid is then reacted with the ethylene oxide, which can, following heating, be metered into the pressurized container in portions via a syphon.

The molar reaction ratio of dimer fatty acid to ethylene oxide is preferably in the range from 1:0.5 to 1:6.0, preferably from 1:1 to 1:3.0. The method exhibits particular advantages with regard to selectivity when approximately two moles of ethylene oxide are reacted per mole of dimer fatty acid (molar feed ratio 1:2).

The ethoxylation can be carried out at temperatures in the range from 100° C. to 150° C. The ethoxylation is preferably carried out at 110 to 140° C. and in particular at 115 to 125° C. During the ethoxylation, autogenous pressures in the range from 1 to 5 bar, preferably in the range from 2 to 4 bar, are recommended. When the reaction is complete, it is advisable to stir the mixture to complete the conversion for a certain period of time at room temperature and the autogenous pressures (15 to 90 min). The autoclave is then cooled and decompressed, and the product, if desired, is treated with acids such as, for example, lactic acid or phosphoric acid, in order to neutralize the basic catalyst.

What has been said above in relation to the pure ethoxylation also applies analogously to the pure propoxylation and for the mixed ethoxylation and propoxylation reaction, where, in the case of the latter, either a mixture of ethylene oxide and propylene oxide can be reacted with the dimer fatty acids, or firstly ethylene oxide and then propylene oxide or vice versa, as desired. In principle, the method according to the invention is also suitable for the alkoxylation with butylene oxide, although preference is given to carrying out the alkoxylation with ethylene oxide and/or propylene oxide, in particular only with ethylene oxide.

Using the method according to the invention, alkylene glycol esters of dimer fatty acids are obtained in good yields, it having been possible, in particular, to reduce the proportion of diesters, as reaction products, which form by reaction of two dimer fatty acids with one another, which is particularly undesirable in the case of high molecular weight dimer fatty acids. Thus, the products prepared by the method according to the invention preferably have a monoester content above 85% by weight, in particular above 90% by weight, and a diester content below 7% by weight, preferably below 5% by weight, based on the process product. The remainder to 100% by weight is unreacted residual acid.

The alkylene glycol esters produced as the main product by the method according to the invention can be described in simple terms by the formula (I)

$$H-(OR)_n OOC-R^1-COO(RO)_n-H \tag{I}$$

in which $R^1$ is a hydrocarbon radical of a dimer fatty acid having 24 to 44 carbon atoms, and R are in each case independently of one another alkyl radicals having 2 or 3 carbon atoms, in particular $CH_2CH_2$, $CHCH_3CH_2$ and/or $CH_2CHCH_3$, and n is in each case approximately the same number in the range from 0.25 to 3.0.

This formula is simplified in as much as it has been assumed that the dimer fatty acids used are exclusively dimeric carboxylic acids. However, as described above, the dimer fatty acids, being technical-grade mixtures, also contain proportions of monomeric and trimeric and other polymeric carboxylic acids. Since the dimer fatty acids preferred for the purposes of the invention are present as the main constituent, the formula (I) stands for compounds which are present as the main constituent in the products produced by the method according to the invention.

EXAMPLES

Example 1

An autoclave was charged with 865.5 g (1.5 mol) of dimer fatty acid (prepared by oligomerizing technical-grade oleic acid; monomer content 9% by weight, dimer content 77% by weight, polymer content 14% by weight, acid number 189-197; saponification number 195, molecular weight about 577 g/mol), and 5 g of triethanolamine (corresponding to 0.58% by weight, based on dimer fatty acid) were added. The autoclave was alternately evacuated for 30 minutes at 80° C. and 30 mbar and flushed with nitrogen three times in order to remove traces of water which could lead to the formation of polyethylene glycol. After the reaction mixture had been flushed for the last time with nitrogen, the autoclave was sealed and heated to 120° C., and, at a maximum pressure of 5 bar, 132.3 g (3 mol) of ethylene oxide were introduced in portions. When the reaction was complete, recognizable from the fact that the pressure dropped again to a value of 2 bar and then remained constant, the reaction mixture was stirred for 60 min at 120° C. and 5 bar and subsequently cooled and decompressed. The basic catalyst remained in the end product.

A product was obtained which had a dimer ester content with 1 mole of ethylene oxide per carboxyl group of 90.7% by weight, a dimer ester content with more than 1 mole of ethylene oxide per carboxyl group of 2.8% by weight, a proportion of diesters of 3.2% by weight and a residual acid content of 3.1% by weight.

The composition of the product shows that firstly the method according to the invention produces, in high yields, dimer fatty acids which no longer contain unesterified carboxyl groups and, secondly, that the method according to the invention is extremely selective since the majority of the dimer esters are compounds which, per mole of carboxyl group of the dimer fatty acid, have only 1 mole of ethylene oxide- or desired amounts corresponding to the amounts of ethylene oxide used.

Example 2

A dimer fatty acid ester was prepared under the same conditions as described in Example 1, except that the catalyst used was diglycolamine. 1125 g of dimer fatty acid (prepared by oligomerization of linoleic acid with a monomer content of 9% by weight, dimer content of 77% by weight and polymer content of 14% by weight, and an acid number of 124) were reacted in the presence of 6.5 g (0.5% by weight, based on dimer fatty acid) of diglycolamine and 176 g of ethylene oxide. The end product had a dimer ester content of product ethyoxylated with 1 mole of ethylene oxide per carboxyl group of 92% by weight. The acid number was 4.6. The OH number was measured as 160.

What is claimed is:

1. A process for preparing alkylene glycol esters of dimer fatty acids according to the general formula (I):

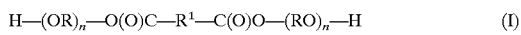

$$H\text{—}(OR)_n\text{—}O(O)C\text{—}R^1\text{—}C(O)O\text{—}(RO)_n\text{—}H \quad (I)$$

wherein $R^1$ represents a hydrocarbon radical of a dimer fatty acid having from about 24 to about 44 carbon atoms, and each R independently represents an alkyl radical having from about 2 to about 3 carbon atoms, and each n independently represents a number of from about 0.25 to about 3.0; said process comprising:
   (a) providing dimer fatty acids;
   (b) providing an alkylene oxide; and
   (c) reacting the dimer fatty acids and the alkylene oxide, in the presence of a catalytically-effective amount of at least one alkanolamine.

2. The process according to claim 1, wherein the dimer fatty acids are prepared by oligomerization of technical-grade unsaturated fatty acids having from about 12 to about 22 carbon atoms.

3. The process according to claim 2, wherein the technical-grade unsaturated fatty acids comprise oleic acid.

4. The process according to claim 1, wherein the alkylene oxide comprises ethylene oxide.

5. The process according to claim 1, wherein the dimer fatty acids are reacted with the alkylene oxide in a molar ratio of from about 1:0.5 to about 1:6.0.

6. The process according to claims 1, wherein the dimer fatty acids are reacted with the alkylene oxide in a molar ratio of from about 1:1 to about 1:3.0.

7. The process according to claim 1, wherein the at least one alkanolamine comprises triethanolamine.

8. The process according to claim 1, wherein the at least one alkanolamine is present in an amount of from about 0.05% to about 5% by weight, based on the amount of dimer fatty acids.

9. The process according to claim 7, wherein the triethanolamine is present in an amount of from about 0.05% to about 5% by weight, based on the amount of dimer fatty acids.

10. The process according to claim 1, wherein the dimer fatty acids are reacted with the at least one alkylene oxide at temperatures of from about 110° C. to about 150° C.

11. The process according to claim 1, wherein the dimer fatty acids are reacted with the at least one alkylene oxide at temperatures of from about 115° C. to about 125° C.

12. The process according to claim 1, wherein the dimer fatty acids are reacted with the at least one alkylene oxide at autogenous pressures of from about 1 to about 5 bars.

13. The process according to claim 1, wherein the dimer fatty acids are reacted with the at least one alkylene oxide at autogenous pressures of from about 2 to about 4 bars.

14. The process according to claim 1, wherein the dimer fatty acids are reacted with the at least one alkylene oxide at temperatures of from about 110° C. to about 150° C. and at autogenous pressures of from about 2 to about 4 bars.

15. The process according to claim 14, wherein the at least one alkanolamine is present in an amount of from about 0.05% to about 5% by weight, based on the amount of dimer fatty acids.

16. The process according to claim 14, wherein the dimer fatty acids are prepared by oligomerization of technical-grade unsaturated fatty acids having from about 12 to about 22 carbon atoms.

17. The process according to claim 15, wherein the dimer fatty acids are prepared by oligomerization of technical-grade unsaturated fatty acids having from about 12 to about 22 carbon atoms.

18. The process according to claim 16, wherein the dimer fatty acids are reacted with the alkylene oxide in a molar ratio of from about 1:1 to about 1:3.0.

19. The process according to claim 17, wherein the dimer fatty acids are reacted with the alkylene oxide in a molar ratio of from about 1:1 to about 1:3.0.

20. A process for preparing alkylene glycol esters of dimer fatty acids according to the general formula (I):

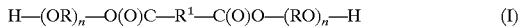

$$H\text{—}(OR)_n\text{—}O(O)C\text{—}R^1\text{—}C(O)O\text{—}(RO)_n\text{—}H \quad (I)$$

wherein $R^1$ represents a hydrocarbon radical of a dimer fatty acid having from about 24 to about 44 carbon atoms, and each R independently represents an alkyl radical having from about 2 to about 3 carbon atoms, and each n independently represents a number of from about 0.25 to about 3.0; said process comprising:
   (a) providing dimer fatty acids, wherein the dimer fatty acids are prepared by oligomerization of technical-grade unsaturated fatty acids comprising oleic acid;
   (b) providing an alkylene oxide comprising ethylene oxide; and
   (c) reacting the dimer fatty acids and the alkylene oxide, in the presence of triethanolamine present in an amount of from about 0.05% to about 5% by weight, based on the amount of dimer fatty acids, at temperatures of from about 110° C. to about 150° C. and at autogenous pressures of from about 1 to about 5 bars, wherein the dimer fatty acids are reacted with the alkylene oxide in a molar ratio of from about 1:1 to about 1:3.0.

* * * * *